United States Patent [19]

Chen et al.

[11] Patent Number: 5,270,332
[45] Date of Patent: Dec. 14, 1993

[54] CHOLESTERAL LOWERING AGENTS

[75] Inventors: Shieh-Shung T. Chen, Morganville; Leeyuan Huang, Watchung; John G. MacConnell, Westfield; Jon D. Polishook, Scotch Plains; Raymond F. White, Englishtown, all of N.J.

[73] Assignee: Merck & Co., Inc., Rahway, N.J.

[21] Appl. No.: 934,134

[22] Filed: Aug. 21, 1992

[51] Int. Cl.$^5$ .................. A61K 31/335; C07D 319/08
[52] U.S. Cl. ...................................... 514/452; 549/363
[58] Field of Search .......................... 549/363; 514/452

[56] References Cited

U.S. PATENT DOCUMENTS

| | | | |
|---|---|---|---|
| 5,026,554 | 6/1991 | Bartizal et al. | 549/363 |
| 5,055,487 | 10/1991 | Bartizal et al. | 514/452 |
| 5,096,923 | 3/1992 | Bergstrom et al. | 514/452 |
| 5,102,907 | 4/1992 | Bergstrom et al. | 549/363 |
| 5,132,320 | 7/1992 | Bergstrom et al. | 514/452 |

FOREIGN PATENT DOCUMENTS

| | | |
|---|---|---|
| 494622 | 7/1992 | European Pat. Off. |
| WO92/12156 | 7/1992 | PCT Int'l Appl. |
| WO92/12159 | 7/1992 | PCT Int'l Appl. |
| WO92/12160 | 7/1992 | PCT Int'l Appl. |
| WO92/16530 | 10/1992 | PCT Int'l Appl. |

OTHER PUBLICATIONS

Baxter et al., *J. Biol. Chem.* vol. 267, 11705–11708 (1992).
Sidebottom et al., *J. Antibiotics*, 45, 648–657 (May 1992).

*Primary Examiner*—Nicky Chan
*Attorney, Agent, or Firm*—Catherine A. Dolan; Melvin Winokur; Paul D. Matukaitis

[57] ABSTRACT

This invention relates to compounds of structural formula (I):

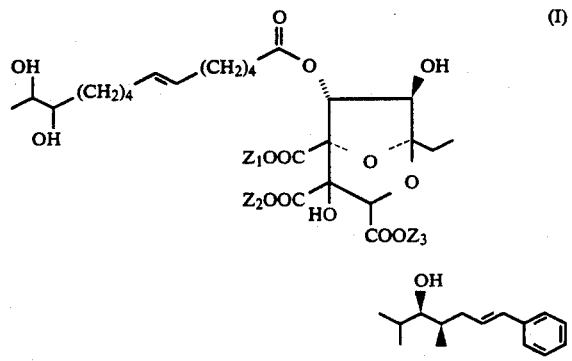

which are squalene synthase inhibitors and thus useful as cholesterol lowering agents. The compounds also exhibit antifungal activity and are inhibitors of farnesyl-protein transferase.

7 Claims, No Drawings

CHOLESTERAL LOWERING AGENTS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR ® (lovastatin) and ZOCOR ® (simvastatin), now commercially available, are members of a group of very active antihypercholesterolemic agents that function by limiting cholesterol biosynthesis by inhibiting the enzyme, HMG-CoA reductase.

Squalene synthase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol, and isopentyl t-RNA.

Previous efforts at inhibiting squalene synthase have been employed pyrophosphate or Pyrophosphate analog containing compounds such as those described in P. Ortiz de Montellano et al. *J. Med. Chem.* 20, 243 (1977) and E. J. Corey and R. Volante, *J. Am. Chem. Soc.*, 98, 1291 (1976). S. Biller (U.S. Pat. No. (4,871,721) describes isoprenoid (phosphinylmethyl) phosphonates as inhibitors of squalene synthase.

Recently certain nonphosphorous containing inhibitors of squalene synthase have been isolated as natural products. For example, U.S. Pat. No. 5,055,487 issued Oct. 8, 1991 describes compounds of structural formula (III):

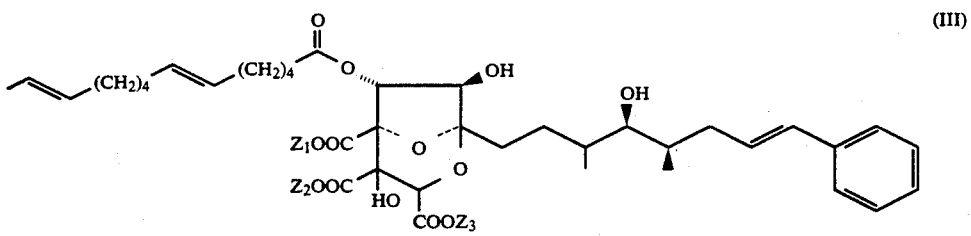

and their use as cholesterol lowering agents and antifungal agents. In particular, this patent discloses preparation of the compound wherein $Z_1$, $Z_2$ and $Z_3$ are each hydrogen (i.e., compound II) by aerobic fermentation procedures employing fungal cultures MF5447 (ATCC 20985) and MF5466 (ATCC 20989). MF5447 is that of a coprophilous fungus, *Sporormiella intermedia*, isolated from cottontail rabbit dung (Arizona). MF5466 is that of coprophilous fungus, a bitunicate ascomycete, isolated from big horn sheep dung (Tuscon, Ariz.). A need still remains for a more effective squalene synthase inhibitor, i.e., one that provides a greater antihypercholesterolemic effect and exhibits a good safety profile.

The present invention is directed to biotransformed analogs of the above-noted natural products.

DETAILED DESCRIPTION OF THE INVENTION

The present invention is directed to novel compounds of structual formula (I) which are squalene synthase inhibitors:

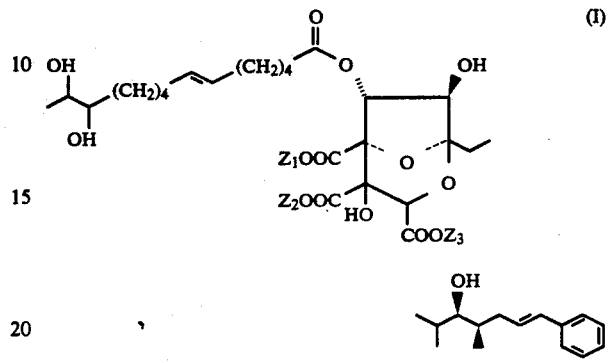

wherein $Z_1$, $Z_2$ and $Z_3$ are each independently selected from the group consisting of
(a) H;
(b) $C_{1-5}$ alkyl;
(c) $C_{1-5}$ alkyl substituted with a member of the group consisting of
 (i) phenyl;
 (ii) phenyl substituted with methyl, methoxy, halogen (Cl, Br, I, F) or hydroxy;
 (iii) $C_{1-5}$ alkylcarbonyloxy; or a pharmaceutically acceptable salt thereof.

In one class of this invention is the compound of formula (I) wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound A.

In a second class are the compounds of formula (I) in which one or more of $Z_1$, $Z_2$ or $Z_3$ is $C_{1-5}$ alkyl or $C_{1-5}$ alkyl substituted with $C_{1-5}$ alkylcarbonyloxy. In a first subclass are those compounds wherein at least one of $Z_1$, $Z_2$ and $Z_3$ is $C_{1-5}$ alkyl substituted with $C_{1-5}$ alkylcarbonyloxy. Further illustrating this subclass are those compounds wherein at least one of $Z_1$, $Z_2$ and $Z_3$ is $-CH_2-O-COC(CH_3)_3$. In a second subclass are those compounds in which one or more of $Z_1$, $Z_2$ and $Z_3$ is $C_{1-5}$ alkyl. Exemplifying this subclass is the compound wherein $Z_1$, $Z_2$ and $Z_3$ are each methyl. This compound is hereafter referred to as Compound B.

Compound A is prepared by a biotransformation of a compound of structural formula (II):

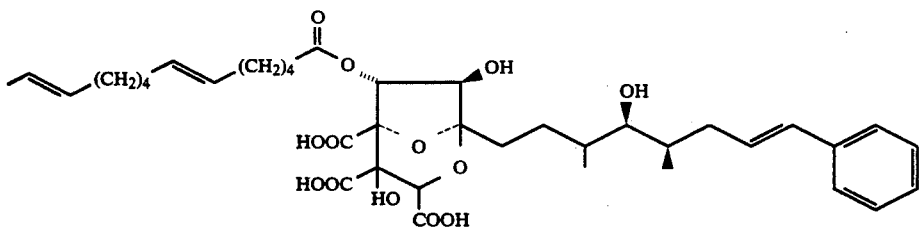

by incubation of fungal culture MF5740 in a nutrient medium in the presence of compound (II). Although the use of this microorganism is specifically described herein, mutants of MF5740 are also capable of producing compounds of this invention. These mutants have essentially the same characteristics as MF5740. The term "mutant" refers to an MF5740 organism in which some gene of the genome is modified, leaving the gene or genes responsible for the organism's ability to produce compounds of formula (I) in recoverable amounts functional and heritable.

The 3, 4 and 5 carboxy groups of Compound A may be esterified with the appropriate alkylating agent and DBU. By using 1, 2 or 3 equivalents of the appropriate alkylating agent, Compound A may be selectively esterified. However, esterification may lead to a mixture of mono, di and triesters and these may be separated, by preparative HPLC using a C-8 reverse phase column and a gradient solvent of water/acetonitrile.

The culture MF5740 is that of a previously unknown strain of Asteroma sp. (Ceolomycetes, Deuteromycotina) which was isolated from an unknown source. This culture has been deposited with the American Type Culture Collection at 12301 Parklawn Drive, Rockville, Md. 20852 as ATCC 74179 under the terms of the Budapest Treaty.

A biologically pure culture of MF5740, as claimed herein, is defined as being originally isolated from the natural environment and free of viable contaminating microorganisms. A culture of MF5740, as claimed herein, is defined as being originally isolated from the natural environment and free of viable contaminating microorganisms that would be deleterious to the formation of compounds of formula (I).

The organism of the present invention is classified as an Asteroma sp. (Coelomycetes, Deuteromycotina). Diagnostic features of the genus Asteroma include the production of numerous pycnidia to form a stroma, simple, discrete, conidiogenous cells and hyaline, 1-celled, cylindrical conidia. The culture MF5740 exhibits all of these characteristics and thus agrees well with the generic concept of Asteroma sp., (B. S. Sutton, *The Coelomycetes*, Commonwealth Mycological Institute, Kew (1980)). However, the characters observed do not fit exactly with any of the species presently described by Sutton. The present system of taxonomy for the class Coelomycetes is based largely on micro- and macroscopic characteristics observed in nature; therefore, it is not certain that those characters seen in nature will be the same as those seen in artificial cultural conditions.

The culture MF5740 exhibits the following morphological features.

Colonies attaining a diameter of 24 mm after 1 week on potato-dextrose agar (Difco) at 25° C. and 50% relative humidity in 12 hour fluorescent light/12 hour dark daily cycle. Aerial mycelium cottony, sparse, white, culture mat appressed, sulcate, appears thickly woven, dense, olivaceous green, Buffy Citrine (capitalized color names from Ridgway, R., *Color Standards and Nomenclature*, Washington, D.C. 1912), Saccardo's Olive, Citrine, margin entire, hyaline, reverse gray, Olive Gray, Deep Olive Gray, exudate and pigment absent.

Colonies attaining a diameter of 21 mm after 1 week on oatmeal agar (Difco) at 25° C. and 50% relative humidity in 12 hour fluorescent light/12 hour dark daily cycle. Culture mat cottony, green-gray, Yellowish Olive, Kronberg's Green, colony center flat, appressed, abundant conidiomata, margin hyaline, entire, reverse, exudate and pigment absent.

Colonies attaining a diameter of 20 mm on corn meal agar (Difco) after 1 week at 25° C. and 50% relative humidity in 12 hour fluorescent light/12 hour dark daily cycle. Culture mat flat, appressed, light olive green, Tea Green, conidiomata confluent at colony center, sparser towards edge, reverse, exudate and pigment absent.

Mycelium hyaline, thin walled, septate, 2.0–3.0 μm wide, guttulate, branched. Conidiomata pycnidial, 120–160×100–120 μm, spherical to ovate, ostiolate, appears to form stroma when abundant, exudes conidia as a white, mucoidy mass. Conidiogenous cells phialidic, 4.8–6.4×3.2–4.8 μm, enteroblastic, discrete, ampulliform to lageniform, collarette minute, hyaline, smooth. Conidia hyaline, smooth, 4.5–5.6×1.6–2.4 μm, cylindrical to subcylindrical to slightly fusiform, straight to slightly curved, refractive bodies at each end.

Compounds of formula (I) can be obtained by culturing the above noted microorganism in the presence of an appropriate concentration of substrate compound (i e., Compound II) in an aqueous nutrient medium containing sources of assimilable carbon and nitrogen, preferably under submerged aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts, and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging from 0.2 to 90 percent by weight of the medium.

The carbon and nitrogen sources are generally employed in combination, but need not be in pure form. Less pure materials which contain traces of growth factors, vitamins, and mineral nutrients may also be used Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added especially if the culture medium foams seriously.

The preferred process for production of compounds of this invention consist of inoculating spores or mycelia of the producing organism into a suitable medium and then cultivating under aerobic condition.

The fermentation procedure generally is to first inoculate a preserved source of culture into nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably between 200 and 220 rpm. Seed flasks are incubated over a period of 2 to 10 days, preferably 2 to 4 days. When growth is plentiful, usually 2 to 4 days, the culture may be used to inoculate transformation medium flasks. A second stage seed growth may be employed, particularly when going into larger vessels. When this is done, a portion of the culture growth is used to inoculate a second seed flask incubated under similar condition but employing shorter time.

After inoculation, the transformation medium is incubated and then substrate compound is added in an appropriate concentration. The resulting transformation flasks are subsequently incubated for 2 to 10 days, preferably 4 to 6 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 27° C. The pH of the nutrient medium suitable for Producing the active compounds is in the range of 3.55 to 8.5, most preferably 5.0 to 7.5. After the appropriate period for the production of the desired compound, fermentation flasks are harvested and the active compound isolated.

The active compounds may then be isolated using the following general isolation procedure. A water miscible solvent such as, but not limited to, methanol, ethanol, acetone, acetonitrile, or any suitable mixture thereof, is added to the whole broth. The mixture is filtered and the filter cake washed with additional water miscible solvent (or solvent mixture). A preferred water miscible solvent is methanol.

The filtrates are combined and the organic solvent removed in vacuo to yield an aqueous residue. The aqueous residue is acidified with concentrated $H_3PO_4$ and then extracted with a water immiscible solvent. Suitable water immiscible solvents include, but are not limited to, ethyl acetate, methyl ethyl ketone, dichloromethane, or a suitable mixture thereof. Preferably, ethyl acetate is used. The organic phase is separated, dried over a neutral drying agent such as sodium sulfate, barium perchlorate, calcium chloride, etc., then filtered and evaporated to dryness. A preferred drying agent is sodium sulfate.

The residue is redissolved in a small amount of MeOH-HCOOH (9:1) suitable for a first chromatographic step. The sample is subjected to low pressure liquid chromatography using a column packed with a washed neutral crosslinked polymer resin equilibrated with deionized (DI) water or 1% solution of HCOOH in DI water Suitable resins include but are not limited to, HP-20 and XAD-2; preferably HP-20 is used as the resin. The chromatogram is developed in a stepwise gradient mode using ca. 2 column volumes of each DI water and water-acetonitrile mixtures of increasing acetonitrile content (10%, 20%, 30%, etc.) also containing 1% HCOOH. The selection of the fractions containing the metabolite of interest is based on analytical HPLC. The selected fractions are pooled and stripped from acetonitrile in vacuo.

The remaining aqueous solution is again acidified, extracted with a water immiscible solvent, the organic layer separated, dried, and evaporated to dryness as described above. The residue is redissolved in a minimum amount of MeOH to be used as feed for a second chromatographic step, i.e., preparative HPLC. The prep HPLC is performed on any of the commercially available C8 bonded phase silica gel with gradient elution. A preferred silica gel column is Beckman Ultrasphere, 10×250 mm. A suitable solvent system is water-acetonitrile mixture also containing 1% HCOOH or 0.1% TFA. The elution is monitored by means of a UV detector set at 252 nm. The highly pure product is obtained by first continuously displacing the eluting solvent with MeOH during the evaporation in nitrogen stream, and at the end, by also removing the methanol in the same way.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthase which comprises the administration to a subject in need of such treatment a nontoxic therapeutically effective amount of compound represented by structural formula (I) and Pharmaceutically acceptable salts thereof. Specifically, the compounds of this invention are useful in treating disease conditions such as, but not limited to, hypercholesterolemia which result from the action of the enzyme squalene synthase. They may be administered orally or parenterally in the form of a capsule, a tablet, an injectable preparation or the like It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The squalene synthase assay using rat liver microsomes is described below:

Preparation of Rat Liver Microsomes

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine ethanesulfonic acid), 5 mM EDTA (ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one fifth the volume of the original homogenate. This microsomal preparation has a protein concentration of about 7 mg/ml. The microsomal suspensions were stored in aliquots at −70° C. Squalene synthase activity in these aliquots is stable for at least several months.

Squalene Synthase Assay

Reactions were performed in 13×100 mm test tubes. If the squalene epoxidase inhibitor is not used, the assay must be performed under anaerobic conditions and screw top test tubes are used. A batch assay mix was prepared from the following solution:

| | µl per assay |
|---|---|
| 1. 250 mM Hepes pH 7.5 | 20 |
| 2. KF or NaF 110 mM | 10 |
| 3. MgCl$_2$ 55 mM | 10 |
| 4. Dithiothreitol 30 mM | 10 |
| 5. NADPH 10 mM (made fresh) | 10 |
| 6. [$^3$H]farnesyl-pyrophosphate 15 Ci/mmole, 33 µM | 1.0 |
| 7. Squalene epoxidase inhibitor (optional) | 2 |
| 8. H$_2$O 50 µg/ml | 25 |

If a squalene epoxidase inhibitor (ingredient 7, above) is not used, the assay mix is degassed under a vacuum and flushed with N$_2$. Solutions of the squalene synthase inhibitors were prepared either in DMSO or MeOH and a 1:120 dilution, for example, of the microsomal protein was made with the original homogenizing buffer. For each reaction, 88 µl of the assay mix was taken with 2 µl of an inhibitor solution (DMSO or MeOH in the controls), warmed to 30° C. in a water bath and then the reaction was initiated by the addition of 10 µl of the 1:120 dilution of microsomal protein (0.6 µg protein total in the assay). The reactions were stopped after 20 minutes by the addition of 100 µl of a 1:1 mix of 40% KOH with 95% EtOH, and cooled. Two ml of heptane was added and the mix was vortexed. Activated alumina (0.5 g) was then added, the mix vortexed again, the alumina allowed to settle and 0.7 ml of the heptane layer was removed. Five ml of scintillation fluid was added to the heptane solution and radioactivity was determined by liquid scintillation counting.

The intrinsic squalene synthase inhibitory activity of representative compounds of this invention was also measured by the standard in vitro protocol described below:

PREPARATION OF HUMAN HepG2 cell ENZYME

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non essential amino acids, sodium pyruvate, and 10% fetal bovine serum. The medium was changed twice weekly. A confluent monolayer was achieved in 1 week. The growth medium was prepared as listed below:

| Solution | Volume (ml) |
|---|---|
| 1. MEM (Gibco #320-1090AK) With Earle's salts and L-glutamine | 1000 |
| 2. Penicillin (10,000 units/mL), streptomycin (10,000 mg/mL), Gibco #600-5140 PG | 10 |
| 3. MEM sodium pyruvate, 10 mM (100X) Gibco #320-1140 | 10 |
| 4. MEM nonessential amino acids, 10 mM (100X) Gibco #320-1140AG | 10 |
| 5. L-glutamine, 200 mM (100X), Gibco #320-5030AG | 10 |
| 6. Hyclone fetal bovine serum, defined, Hyclone #A-111-L | 100 |

SUBCULTURE PROCEDURE: The medium was removed and washed with PBS (Phosphate-Buffered Saline 15.6 mM. pH 7.0). Fresh trypsin (0.25%)-EDTA (0.02%) with Hank's Balanced Salt solution was added and the flask was allowed to stand for a minute before the trypsin was removed. The flask was incubated at 37° C. until cells detached. Fresh medium was added and the cells were dispersed and dispensed into new flasks. Subcultivation ration: 1:6.

PREPARATION OF DELIPIDATED SERUM: Fetal calf serum (100 ml) and CAB-O-SIL ® (2 grams)

were stirred overnight at 4° C. and centrifuged at 16,000 rpm for 5 hours. The supernatant was filtered and the serum was stored at 4° C.

Fortyeight hours prior to harvest, cells grown in MEM with 10% Fetal Calf serum were switched to MEM with 10% delipidated serum HARVEST: The medium was removed and the cells were washed with PBS. Fresh trypsin (0.25%)-EDTA (0.02%) with Hank's Balanced Salt solution was added and the cells allowed to stand for 1 minute and removed. The flask was incubated at 37° C. until the cells detached. MEM medium (6 ml/flask) was added to suspend cells and combined into a centrifuge tube. The cells were spun at 1,000 rpm for 5 minutes. The cell pellet was resuspended in PBS and recentrifuged. Cells 1 were counted ($2.5 \times 10^9$ yield from 18 flasks (75cm$^2$)), and resuspended in 10 ml of 50 mM HEPES (N-[2-Hydroxyethyl]piperazine-N'-[2-ethane sulfonic acid]) containing 5 mM $MgCl_2$, 2 mM $MnCl_2$, 10 mM DTT, pH 7.5 (enzyme suspension buffer).

CELL EXTRACTS: The cell suspension was sonicated (probe sonicator setting #60, pulse) on ice for 2 minutes. After a 1 minute cooling on ice, the sonication was repeated until greater than 90% of the cells were broken as observed microscopically. The cell suspension was centrifuged for 10 minutes at $12,000 \times g$ and the supernatant was transferred to a clean tube and centrifuged at $20,000 \times g$ for 20 mins. The HepG2 enzyme preparation was centrifuged at $100,000 \times g$ to separate the cytosol and microsomal enzymes. The resulting pellet from the $100,000 \times g$ centrifugation, containing the squalene synthase, was resuspended in 5 ml of enzyme suspension buffer. The enzyme suspension was diluted and used to perform the squalene synthase assay using 3 μM $^3$H-farnesyl pyrophoshate as the substrate.

Squalene Synthase Assay

Reactions were performed in 1.2 ml polypropylene tube strips of 8. Buffer mixture and substrate mixture for the assay were prepared from the following solution:

Buffer mixture contains 270 mM HEPES, pH 7.5, 20 mM Potassium fluoride and 5.4 mM Dithiothreitol (DTT). 55 μL of this mixture was used per assay. The final concentration of HEPES, KF and DTT in the assay are 150 mM, 11 mM and 3 mM respectively.

Substrate mixture:

| Stock concentration | μl used per assay | Final concentration |
|---|---|---|
| 1. $MgCl_2$, 55 mM | 10 | 5.5 mM |
| 2. NADPH, 10 mM (made fresh) | 10 | 1 mM |
| 3. Squalene Epoxidase inhibitor, Banyu FW-439H, 0.5 mg per ml | 0.02 | 0.1 μg per ml |
| 4. $^3$H-farnesyl-pyrophosphate, 25 μM, 20 Ci per mole | 0.24 | 0.06 μM |
| 5. Farnesyl-pyrophosphate, 3 mM | 0.098 | 2.94 μM |
| 6. Water | 9.63 | |

For each reaction, 55 μL of buffer mixture was taken with 5 μL of an inhibitor solution in MeOh and 10 μL of diluted enzyme (the final protein concentration of enzyme in the assay is 1.2 μg per ml.). The reaction was initiated by the addition of 30 μl of substrate solution and the mixture was incubated at 30° for 20 minutes. The reactions were stopped by the addition of 100 μl of 95% EtOH, vortexed, and 100 μl of a suspension of 1 gram per ml of Bio-RAD AG 1×8 resin (400 mesh, Chloride form) was then added, vortexed. 800 μl of heptane was added to each tube strip and the strips were capped and vortexed for 10 minutes 400 μl of heptane layer was then removed into a minivial and mixed with 2.5 ml of scintillation fluid and the radioactivity was determined by liquid scintillation counting. The controls were run with 5 μl of MeOH and blanks were run with the addition of 100 μl of 95% EtOH to denature the enzyme before the addition of the substrate mixture to the assay tube.

Percent inhibition is calculated by the formula:

$$1 - \frac{[\text{Sample} - \text{Blank}]}{[\text{Control} - \text{Blank}]} \times 100$$

$IC_{50}$ values were determined by plotting the log of the concentration of the test compound versus the percentage inhibition. The $IC_{50}$ is the concentration of inhibitor that gives 50% inhibition as determined from these plots.

Below are $IC_{50}$'s representative of the inherent squalene syntase inhibitory activity of the compound of the present invention.

| | SQUALENE SYNTHASE ACTIVITY | |
|---|---|---|
| Compound | Human Enzyme $IC_{50}$ (nM) | Rat Liver Enzyme $IC_{50}$ (nM) |
| A | 31 | 5.6 |

The compounds of the present invention are also useful in inhibiting farnesyl-protein transferase.

The Ras gene is found activated in many human cancers including colorectal carcinoma, exocrine pancreatic carcinoma, and myloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modification are involved with Ras membrane localization, and all 3 modifications occur at the C-terminus of Ras. The Ras C-terminus contains a sequence motif termed a "CAAX" or "Cys-Aaa[1]-Aaa[2]-Xaa" box (Aaa is an aliphatic amino acid, the Xaa is any amino acid) (Willumsen et al., *Nature* 310:583–586 (1984)). Other proteins having this motif include the Ras related GTP binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57: 1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem* 263:18236 (1989); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62: 81–88 (1990); Schaber et al., *J. Biol. Chem.*, 265:14701–14704 (1990); Schafer et al, *Science*, 249: 1133–1139 (1990); Manne et al., *Proc. Natl. Acad. Sci USA*. 87: 7541–7545 (1990)).

Inhibition of farnesyl-protein transferase and, thereby, of farnesylation of the Ras protein, blocks the ability of Ras to transform normal cells to cancer cells. The compounds of the present invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no-Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634 (1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds are inhibitors of farnesyl-protein transerase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al, ibid; Reiss et al., ibid; Reiss et al., *PNAS*, 88:732–736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are included within this invention.

The intrinsic farnesyl-protein tranferase (FTase) activity of representative compounds of this invention is measured by the assays described below:

RASIT ASSAY I

Farnesyl-protein transferase (Ftase) from bovine brain is chromatographed on DEAE-Sephacel (Pharmacia, 0–0.8 M NaCl gradient elution), N-octyl agarose (Sigma, 0–0.6 M NaCl gradient elution), and a mono Q HPLC column (Pharmacia, 0–0.3 M NaCl gradient). Ras-CVLS at 3.5 $\mu$M, 0.25 $\mu$M [$^3$H]FPP, and the indicated compounds are incubated with this partially purified enzyme preparation.

RASIT ASSAY II

Farnesyl-protein transferase (Ftase) from bovine brain is chromatographed on DEAE-Sephacel (Pharmacia, 0–0.8 M NaCl gradient elution), N-octyl agarose (Sigma, 0–0.6 M NaCl gradient elution), and a mono Q HPLC column (Pharmacia, 0–0.3 M NaCl gradient). Ras-CVLS at 1.0 $\mu$M, 0.5 $\mu$M [$^3$H]FPP, and the indicated compounds are incubated with this partially purified enzyme preparation.

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to Patients for the use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The present compounds also demonstrate broad spectrum antifungal activity as determined by broth and agar dilution methods. The compounds are particularly active towards filamentous fungi and yeasts including *Candida albicans* and *Cryptococcus neoformans*. The sensitivity of filamentous fungi and yeast is determined using inhibitor dilution assays in microtiter format. The compounds are dissolved in DMSO at 2 mg/ml and serially diluted in 0.1 M phosphate buffer, pH 7.0 in the microtiter dish from 100 to 0.006 $\mu$g/ml. A standardized spore suspension for testing the filamentous fungi is prepared by inoculating Antibiotic Medium #3 containing 1.5% agar with spores such that $1.5 \times 10^3$ colony forming units were added per well. The microtiter wells are filled with 50 $\mu$l of buffer containing compound and 50 $\mu$l of inoculated medium.

The sensitivity of yeasts is determined by inoculating yeast nitrogen base containing 1% dextrose (YNB/G) with aliquots of an overnight yeast culture grown in Yeast Morphology (YM) media at 35° C. and diluting in YNB/G to yield a final concentration of $1.5-7.5 \times 10^3$ colony forming units/well. To test the sensitivity of yeast, compound is solubilized in 10 percent aqueous DMSO at 2.56 mg/ml. The compound is diluted serially in YNB/G from 128 to 0.06 $\mu$g/ml and further diluted 1:10 in YNB/G. The wells are filled with 150 $\mu$l of media containing drug. The minimum inhibitory concentration (MIC) is defined as the lowest concentration to prevent growth after an incubation for 42 hours, at 28° C. for the filamentous fungi and 24 to 48 hours, at 35° C. for the yeasts.

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 5 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof to inhibit fungal growth.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of formula I.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| SEED MEDIUM KE | g/L | SOY-GLUCOSE MEDIUM | g/L |
|---|---|---|---|
| Glucose | 1.0 | Glucose | 20.0 |
| Dextrin | 10.0 | Soya Meal | 5.0 |
| Beef Extract | 3.0 | Yeast Autolysate | 5.0 |
| Ardamine pH | 5.0 | NaCl | 5.0 |
| NZ Amine Type E | 5.0 | pH adjusted to 7.0 | |
| MgSo$_4$.7H$_2$O | 0.05 | before autoclaving | |
| K$_2$HPO$_4$ | 0.3 | | |
| CaCO$_3$ | 0.3 | | |
| pH adjusted to 7.1 | | | |
| before autoclaving | | | |

EXAMPLE 1

Preparation of Compound A

A. Culturing MF5740

A frozen vial of culture MF5740 was used to inoculate a 250 ml baffled shake flask containing 50 ml of previously autoclaved (i.e., sterilized) seed medium KE. The seed was incubated in the seed medium at 27° C. for 48 hours on a rotary shaker operating at 220 rpm. A 2.5 ml aliquot of the resulting seed medium was then used to inoculate each of twenty 250 ml non-baffled shake flasks, each flask containing 50 ml of previously autoclaved Soy-glucose medium used as transformation medium. Substrate Compound II was added, after 24 hours incubation, as a dimethylsulfoxide solution to achieve a final concentration of 0.05 mg/ml in each flask. The resulting transformation flasks with their contents were subsequently incubated for 4 days at 27° C. on a rotary shaker operating at 220 rpm. The resultant broths were examined for biotransformation products by HPLC and combined for isolation and purification.

B. Isolation of Compound A

Methanol (1 volume) was then added to the whole broth from step A, above. The methanol treated flask was filtered and the filter cake washed with methanol. The filtrates were combined and the solvent removed in vacuo. The resultant aqueous residue was acidified with concentrated H$_3$PO$_4$ (0.05 volumes) and extracted with ethyl acetate (EtOAc). The EtOAc layer was separated and evaporated to dryness. The residue was redissolved in a small amount (ca. 5 ml) of MeOH-HCOOH (9:1) which was used for the first chromatographic step, i.e., HP20 chromatography: column 2.5×24 cm washed resin equilibrated with deionized (DI) water. The chromatogram was developed in a stepwise gradient mode using 200 ml each of DI water and water-acetonitrile (CH$_3$CN) mixtures (9:1, 8:2, 7:3 ... 0:10) also containing 1% HCOOH. The metabolite of interest (i.e., compound A) was eluted in fractions between 1050 and 1300 ml; the selection of fractions was based on analytical HPLC. The CH$_3$CN was removed from the pooled fractions in vacuo leaving an aqueous solution. The remaining aqueous solution was acidified with H$_3$PO$_4$ and extracted with EtOAc. The organic layer was separated, dried over NaSO$_4$, filtered and evaporated to dryness.

The residue was redissolved in the smallest possible amount of MeOH and the resultant concentrate used as feed for the second chromatographic step, i.e., preparative HPLC on Beckman Ultrasphere Octyl column (10×250 mm) with gradient elution. Solvent A was 0.1% HCOOH in water; solvent B was 0.1% HCOOH in CH$_3$CN-water (17:3). The gradient program was 30% B for 0–3 minutes, linear gradient to reach 80% B from 3–33 minutes, then 100% B from 33–35 minutes and remaining there for the final 10 minutes. The flow rate was constant at 3.00 ml/minute. Compound A was eluted at 23.0 to 23.4 minutes. Evaporation of the selected fractions provided Compound A:

$^1$H NMR spectrum (400 mHz) (CD$_3$OD, 22° C.): 7.34 (d, J=7.9 Hz, 2H), 7.26 (t, J=7.5 Hz, 2H), 7.15 (t, J=7.4 Hz, 1H), 6.40 (d, J=14.0 Hz, 1H), 6.27 (s, 1H), 6.25 (m, 1H), 5.39 (m, 4H), 5.16 (s, 1H), 3.98 (s, 1H), 3.55 (qn, J=5.8 Hz, 1H), 3.35 (m), 2.30 (m), 1.26–2.10 (m), 1.14 (d, J=6.3 Hz, 3H), 0.99 (d, J=6.1 Hz, 3H), 0.97 (d, J=6.1 Hz, 3H).

EXAMPLE 2

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

EXAMPLE 3

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 4

Preparation of a Potassium Salt

A solution of 0.1 mmol of the free acid of a compound of formula (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields, analogously, mixtures of the mono-potassium, di-potassium and tri-potassium salts whose composition depends upon the exact amount of potassium hydroxide added.

In a similar fashion the sodium and lithium salts can be formed.

EXAMPLE 5

Preparation of a Calcium Salt

A solution of 0.1 mmol of the free acid of a compound of formula (I) in 20 ml of 6:4 methanol/ water is treated with an aqueous solution of 0.1 mmol of calcium hydroxide. The solvents are evaporated to give the corresponding calcium salt.

EXAMPLE 6

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 7

Preparation of a Tris(hydroxymethyl)aminomethane Salt

To a solution of 0.1 mmol of the free acid of a compound of formula (I) in 10 ml of methanol is added from 0.1 to 0.3 mmol of tris(hydroxymethyl)aminomethane dissolved in 10 ml of methanol. Evaporation of the solvent gives a corresponding salt form of the exact composition of which is determined by the molar ratio of amine added. Similarly prepared are the salts of L-ornithine, L-lysine, and N-methylgluacamine.

EXAMPLE 8

Preparation of an L-arginine Salt

A solution of 0.1 mmol of the free acid of a compound of formula (I) in 10 ml of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglucamine.

EXAMPLE 9

Preparation of a Compound B (Method 1)

A solution of 2 mg of Compound A in 5 ml of methanol/ether (1:1) is treated with a slight excess of ethereal diazomethane. After 5 minutes, excess diazomethane is removed and the solvent is evaporated to give Compound B.

EXAMPLE 10

Preparation of Compound B (Method 2)

A solution of 2 mg of Compound A in 0.5 ml of acetonitrile is treated at room temperature with 10 equivalents of DBU and 10 equivalents of methyl iodide. After 2 hours, the reaction is diluted with 10 ml of dichloromethane and washed successively with 10 ml of 0.1 M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give Compound B.

The method of Example 10 is also suitable for the preparation of other ester derivatives such as 1) ethyl and other lower alkyl esters; and 2) benzyl and substituted benzyl esters.

EXAMPLE 11

Preparation of the pivalate ester

To a solution of 2 mg of Compound A in 0 5 ml of refluxing acetonitrile is added 10 equivalents of DBU followed by 10 equivalents of chloromethyl pivalate and a few crystals of sodium iodide. The reaction is stirred overnight, then concentrated in vacuo. The residue is purified by preparative HPLC, using a C-8 reverse phase column and a gradient solvent of water acetonitrile to give the pivalate ester.

What is claimed is:

1. A compound of structural formula (I)

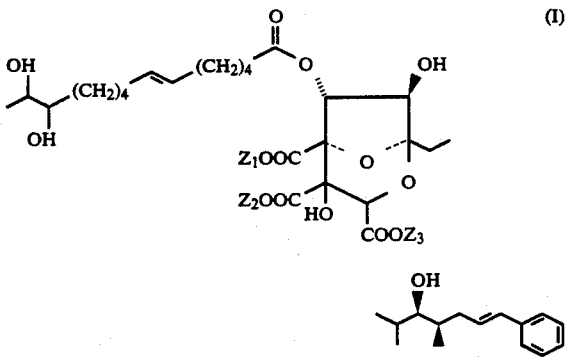

wherein $Z_1$, $Z_2$ and $Z_3$ are each independently selected from the group consisting of:
a) Hydrogen;
b) $C_{1-5}$ alkyl;
c) $C_{1-5}$ alkyl substituted with a member of the group consisting of
   i) phenyl;
   ii) phenyl substituted with methyl, methoxy, halogen (Cl, Br, I, F) or hydroxy; and
   iii) $C_{1-5}$ alkylcarbonyloxy; or a pharmaceutically acceptable salt thereof.

2. A compound of claim 1, wherein $Z_1$, $Z_2$ and $Z_3$ are each independently selected from the group consisting of
(a) H;
(b) $C_{1-5}$ alkyl; and
(c) $C_{1-5}$ alkyl substituted with $C_{1-5}$ alkylcarbonyloxy; or a pharmaceutically acceptable salt thereof.

3. A compound of claim 2, wherein $Z_1 Z_2$ and $Z_3$ are each hydrogen or a pharmaceutically acceptable salt thereof.

4. A pharmaceutical composition comprising a nontoxic therapeutically effective amount of a compound of claim 1 and a pharmaceutically acceptable carrier.

5. A pharmaceutical composition comprising a non toxic therapeutically effective amount of a compound of claim 1 in combination with a pharmaceutically acceptable nontoxic cationic polymer capable of binding bile acids in a non-reabsorbable form in the gastointestinal tract and a pharmaceutically acceptable carrier.

6. A method of treating hypercholesterolemia comprising the administration to a subject in need of such treatment a nontoxic therapeutically effective amount of a compound of claim 1.

7. A method of inhibiting squalene synthase comprising the administration to a subject in need of such treatment a nontoxic therapeutically effective amount of a compound of claim 1.

* * * * *